United States Patent
Garfinkel

(10) Patent No.: US 9,333,054 B1
(45) Date of Patent: May 10, 2016

(54) METHOD AND APPARATUS TO RESTORE A TOOTH IMPLANT IMPAIRED BY PERI-IMPLANTITIS

(71) Applicant: Leonard M. Garfinkel, Aventura, FL (US)

(72) Inventor: Leonard M. Garfinkel, Aventura, FL (US)

(73) Assignee: Leonard M. Garfinkel, Aventura, FL (US)

( * ) Notice: Subject to any disclaimer, the term of this patent is extended or adjusted under 35 U.S.C. 154(b) by 163 days.

(21) Appl. No.: 14/161,746

(22) Filed: Jan. 23, 2014

(51) Int. Cl.
*A61C 8/00* (2006.01)
*A61C 8/02* (2006.01)

(52) U.S. Cl.
CPC ............... *A61C 8/0006* (2013.01); *A61C 8/008* (2013.01); *A61C 8/0068* (2013.01); *A61C 8/0074* (2013.01); *A61C 8/0089* (2013.01)

(58) Field of Classification Search
CPC .... A61C 8/0089; A61C 8/005; A61C 8/0072; A61C 8/0012; A61C 8/0074; A61C 8/008
USPC ........... 433/172–176, 201.1, 202.2, 215, 220, 433/221
See application file for complete search history.

(56) References Cited

U.S. PATENT DOCUMENTS

| | | | |
|---|---|---|---|
| 6,461,160 B1* | 10/2002 | Sutter | 433/173 |
| 8,011,926 B2* | 9/2011 | Ford et al. | 433/174 |
| 8,057,230 B1* | 11/2011 | Folsom, Jr. | 433/174 |
| 8,529,261 B2 | 9/2013 | Schonenberger | |
| 2004/0234925 A1* | 11/2004 | Benhamou | 433/173 |
| 2005/0136378 A1* | 6/2005 | Ennajimi et al. | 433/173 |
| 2009/0036908 A1* | 2/2009 | Zokol et al. | 606/151 |
| 2012/0156645 A1 | 6/2012 | Jacoby | |
| 2013/0344459 A1* | 12/2013 | Collins et al. | 433/174 |

* cited by examiner

*Primary Examiner* — Heidi M Eide
(74) *Attorney, Agent, or Firm* — Malin Haley DiMaggio & Bowen, P.A.

(57) ABSTRACT

The invention is for the repair of a traditional implant previously installed, the implant being of the kind currently manufactured by many implant companies. The invention includes a method and apparatus used to repair a diseased tooth implant having peri-implantitis. A soft thin titanium alloy sleeve having an exterior treated surface for enhancing osseointegration is used for implant surface restoration. The sleeve is initially installed on a dowel. The dowel is necessary to support the thin soft deformable sleeve at all times to prevent its collapse or being crushed. The dowel is also necessary to accomplish the transfer of the sleeve onto the implant surface. The diseased implant is restored by a new surface that enhances osseo-integration provided by the surface restoration sleeve.

5 Claims, 8 Drawing Sheets

METHOD AND APPARATUS TO RESTORE A TOOTH IMPLANT IMPAIRED BY PERI-IMPLANTITIS

CROSS REFERENCE TO RELATED APPLICATIONS

N/A

STATEMENT REGARDING FEDERALLY SPONSORED RESEARCH OR DEVELOPMENT

N/A

BACKGROUND OF THE INVENTION

1. Field of the Invention

This invention relates generally to dental implants, and specifically to a method and apparatus to repair and restore the surface of an implant affected by peri-implantitis (a loss of bone due to disease around an implant) and to allow for the placement of a new surface on an existing implant that will enhance the repair and growth of new bone around an ailing implant.

2. Description of Related Art

Dental implants have been in use in the United States for at least 30 years. In a typical situation the patient will have a loss of a natural tooth due to loss of bone connection. Often an implant will be used as a replacement for a natural tooth.

The tooth implant device includes the implant itself, which is inserted into the bone, an abutment which screws into the implant, and the crown that is placed on the abutment. The invention relates only to the implant itself which integrates into the bone (osseo-intergration).

With the advent of tooth implants, there was a consensus among those practitioners in dentistry responsible for installing implants that the implant was permanent in nature. The patient would benefit by not having to deal with further periodontal disease regarding an implant.

Recently it is being observed by implant practitioners, that a dental implant can suffer from periodontal disease wherein gum and bone separate from the implant surface much in the same way as a natural tooth develops separation when experiencing periodontal disease.

Current implant technology requires the surface of an implant that comes in contact with gum and bone tissue to have very specific characteristics which include sterility and the lack of any toxic substance which would prevent osseo-integration. Once the surface of an implant has been exposed to peri-implantitis, the sterility is gone and the surface is covered with bacteria and all the toxic materials associated with disease. This contamination of the surface then makes repair of the bone around a diseased implant unlikely if not impossible.

The invention described in this patent application provides an apparatus and method that allows the practitioner to repair a previously installed dental implant that has suffered periodontal disease so as to enhance osseo-integration of the patient's bone tissue with the implant exterior surface that has been restored.

In the prior art, the Schonenberger U.S. Pat. No. 8,529,261 shows a device that has nothing to do with the repair of lost bone but that provides a variable seam that is determined at the time of the original placement of the input. The Schonenberger device deals with the anatomy above the bone.

The Jacoby U.S. Patent Publication 2012/0156646 published Jan. 21, 2012 discloses a device to create an implant body with replaceable parts that can be changed. The applicant's invention is completely different because the applicant's invention deals with implants of traditional design already in the mouth that need repair. The Jacoby device has multiple rings of great thickness that comprise the implant body as compared to Applicant's very thin surface restoration sleeve of a given length that can repair any implant body.

BRIEF SUMMARY OF THE INVENTION

An apparatus and associated method for repairing a dental implant previously installed in the patient in which the patient implant is experiencing peri-implantitis including loss of bone tissue from the implant surface. The first step 15 removing by grinding a thin external surface layer that is diseased on the implant in the area to be repaired.

The next steps require the installation of a surface restoration sleeve constructed of a very thin cylinder of titanium material having a specially prepared exterior surface that enhances osseo-integration. Because the wall of the surface restoration sleeve is very thin due to limitations imposed by the size of the implant and the diseased area to be covered and the softness of the titanium alloy required, the installation of press fitting a surface restoration titanium sleeve on the implant requires special steps of manipulation.

The surface restoration sleeve installation in the preferred embodiment requires the use of a dowel. The surface restoration sleeve is initially mounted on a smooth lower exterior surface of the dowel at a laboratory. The dowel containing the surface restoration sleeve is placed in a sterilized environment for delivery to the practitioner who will be repairing the diseased implant. The purpose of the dowel is to facilitate the transfer of the surface restoration sleeve from the dowel to the implant. In addition the dowel also is necessary to support the titanium sleeve or cylinder to prevent the thin wall cylinder from collapsing due to its thinness that predisposes it to losing its shape or becoming squashed.

The next steps are necessary to provide a rigid cylindrical dowel that includes an upper threaded area for receiving a transfer nut and a smooth lower area that initially receives the surface restoration sleeve constructed of a very thin, cylinder of titanium material having a specially prepared exterior surface that enhances osseo-integration of jaw bone tissue with the implant surface. The surface restoration sleeve is pressed around the upper implant surface area initially prepared by grinding off a thin surface layer of the implant to be repaired without anything touching the exterior surface of the restoration sleeve to ensure its continued integrity for osseo-integration.

The dowel is cylindrical in shape and includes two coaxial central hollow passageways of different diameters from end to end that can receive a threaded attachment screw and screw head that is used to firmly attach the dowel to the top of the implant using the threaded female opening already present in the implant. The first larger in diameter coaxial passageway in the dowel is large enough in diameter to receive the attachment screw and the screw head of the attachment screw. The second coaxial passage of smaller diameter can receive the threaded shaft of the attachment screw but is too small in diameter to receive the screw head. The threaded shaft of the attachment screw is much longer than the second dowel passageway having the smaller diameter so that a significant length of the attachment screw shaft that is threaded extends well beyond the end of the dowel that will engage the implant. The extended screw shaft is available to be threadably connected to the existing threaded bore in the top of the implant. The attachment screw is manipulated with a screwdriver to firmly attach the dowel containing surface restoration sleeve to the implant.

Once the dowel housing the restoration sleeve is firmly attached by the threaded screw to the top of the implant, a threaded transfer nut is manually attached to the top outside threaded surface of the dowel. The purpose of the transfer nut is through manual actuation to mechanically force the surface restoration sleeve from the surface of the dowel to the surface of the implant without anything touching the outside surface of the sleeve. By using an appropriate tool such as a wrench that fits the nut snugly, the practitioner can manually rotate the nut mounted on the dowel threaded surface in a downward direction causing the sleeve to move downwardly in a press fit on the implant exterior surface.

The titanium alloy surface restoration sleeve requires extremely stringent handling conditions to prevent bacteria or other material from touching the outer surface of the sleeve while attachment to the implant surface is being conducted. The height or longitudinal length of the sleeve is determined by the amount of bone that has been lost around the diseased implant. The sleeve is mounted to the dowel in a laboratory environment to preserve the biological integrity of the sleeve.

Once the surface restoration sleeve has been firmly pressed onto the exterior surface of the implant in the affected area that has been previously ground smooth, the attachment screw that holds the dowel in place against the implant can be removed, allowing the dowel to be removed.

From this point forward the practitioner would then proceed with surrounding the surface area of the surface restoration sleeve on the implant with the appropriate tissue repair materials to begin the osseo-integration process between gum tissue, bone tissue and the exterior surface of the sleeve surrounding the implant.

One of the key elements of the invention is the surface restoration sleeve which is constructed of materials currently used in an original implant with respect to the stringent requirements on the titanium surface of the implant that engages gum tissue and bone tissue to ensure osseo-integration between the human tissue and the original implant and the surface restoration sleeve used for repair of the diseased implant. It is very important that the inside diameter of the sleeve fits snugly on the outside diameter of the lower half of the dowel and also fit as a pressed fit on the exterior surface of the implant. This fit is accomplished by grinding off the diseased surface layer of the implant so that the resultant implant surface has an outside diameter equal to the inside diameter of the surface restoration sleeve to ensure a press like fit.

It is imperative that during the installation of the surface restoration sleeve that there be zero physical contact with any object including human manual contact with the outer surface of the previously specially treated replacement sleeve.

It is an object of this invention to provide a method of restoring gum tissue and implant osseo-integration to an existing implant that experiences periodontal disease.

It is another object of this invention to provide an apparatus that will deliver the surface restoration sleeve so as to not contaminate it and also to prevent its collapse due to thinness.

PREFERRED EMBODIMENT OF THE INVENTION

Figure 1:
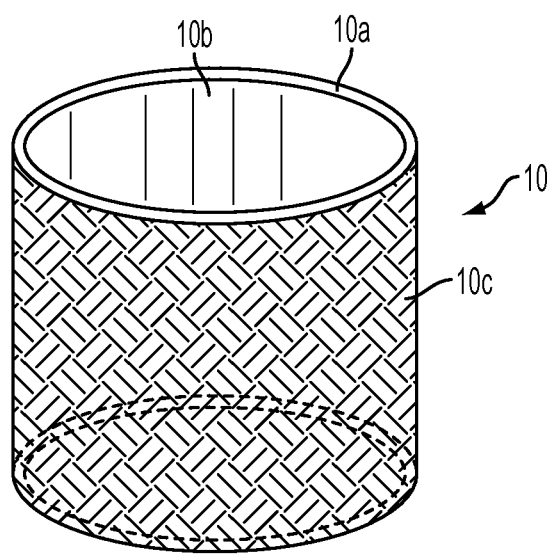
FIG. 1 is a perspective view of a dental implant surface restoration sleeve utilized in the present invention.

Referring now to the drawings and in particular FIG. 1, a soft titanium alloy thin hollow cylindrical sleeve 10 is shown that is ultimately to be placed around the area of the implant to be repaired. The surface restoration sleeve 10 includes a thin cylindrical wall 10a having a predetermined thickness. The inside surface 10b of sleeve 10 is smooth so that the inside surface can be press fitted when installed around the implant surface area to be repaired as explained in greater detail below.

The sleeve 10 has a specially prepared exterior surface 10c that enhances osseo-integration for the growth and attachment of replacement bone tissue to the exterior surface of the sleeve 10c. The process for preparing the exterior surface 10c of sleeve 10 is known in the art. The sleeve 10 is constructed of a specific titanium alloy that is durable but soft. The sleeve surface 10c can be carefully etched to increase surface area. The process to prepare an exterior surface on a new implant for enhanced osseo-intergration is known. It is believed that the same process to alter the surface for enhanced osseo-integration can be accomplished on the surface restoration sleeve 10. It is an important aspect of this invention described herein that the specially treated surface 10c of sleeve 10 cannot be touched by anything from manufacture through installation of the sleeve 10.

The cylindrical wall 10a of the sleeve 10 will of necessity be extremely thin because of the requirements and spatial limitations for proper fit on the exterior of the implant being repaired. An example might be one-half to one millimeter in thickness.

Figure 2:
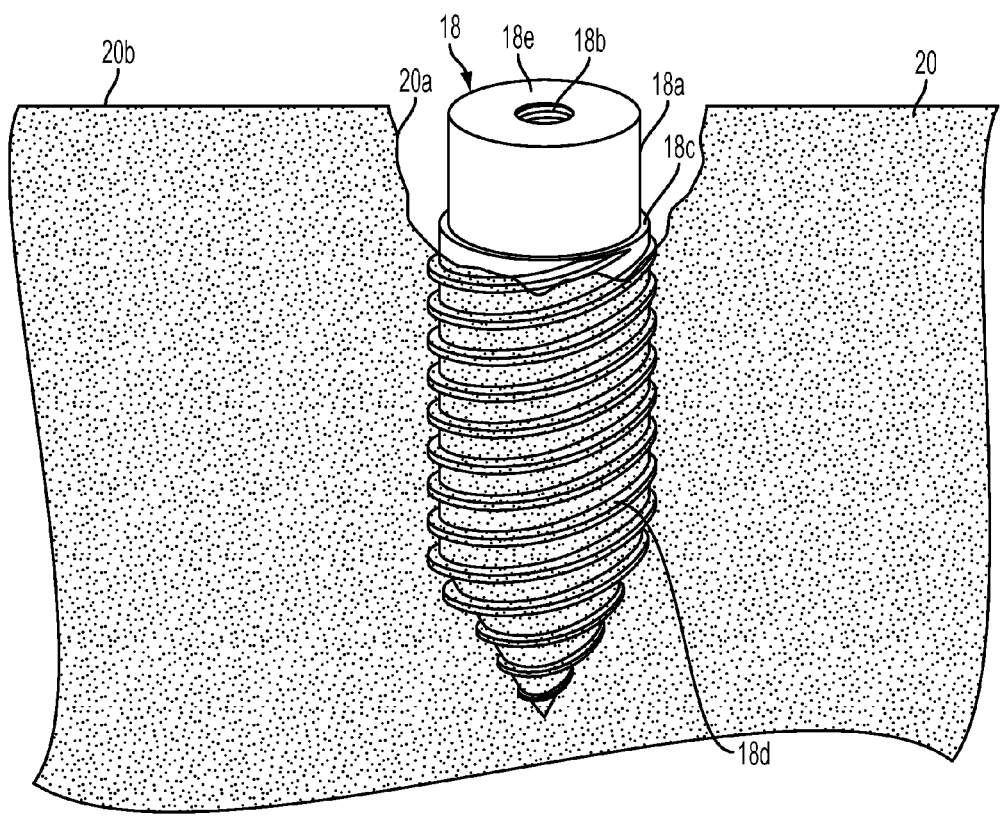
FIG. 2 shows a perspective view of an implant base in a jaw bone, said implant having an upper surface area to be repaired to restore bone loss around the implant.

FIG. 2 shows an implant 18 anchored in a jaw bone 20 having an upper surface 20b. The implant 18 includes a central axial threaded bore that functions as a female threaded fastener 18b. The implant 18 shown in FIG. 2 does not show an abutment or a crown. The implant 18 has a threaded portion 18e that includes threads 18d that anchor the implant base 18 in the jaw bone 20. A jaw bone cavity 20a represents peri-implantitis disease which is the loss of bone connection to the implant upper portion 18a. As shown in FIG. 2, the implant 18 has been treated by the implant practitioner by removing (by grinding) a thin exterior layer of the implant exterior upper surface 18a defined above the remaining peripheral implant wall lip 18c. The result is that the diameter of implant 18 has been slightly reduced around the upper area 18a so that the upper portion 18a of implant 18 can receive a surface restoration sleeve 10 shown in FIG. 1. The grinding action by the practitioner on the surface 18a of implant 18 will also produce a diameter of the implant 18 that is uniformly round and fits the inside diameter of the sleeve 10 that is to be press fitted onto the implant 18.

Figure 4:
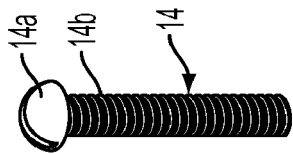
FIG. 4 shows a perspective view of an attaching screw used to attach the dowel shown in FIG. 3A and FIG. 3B to a dental implant to be repaired as shown in FIG. 2.
Figure 3B:
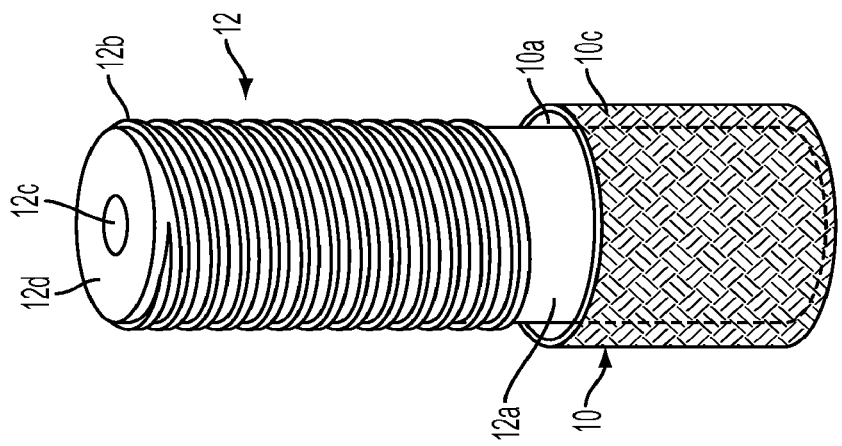
FIG. 3B shows a perspective view of the dowel in FIG. 3A that includes a surface restoration sleeve shown in FIG. 1.
Figure 3A:
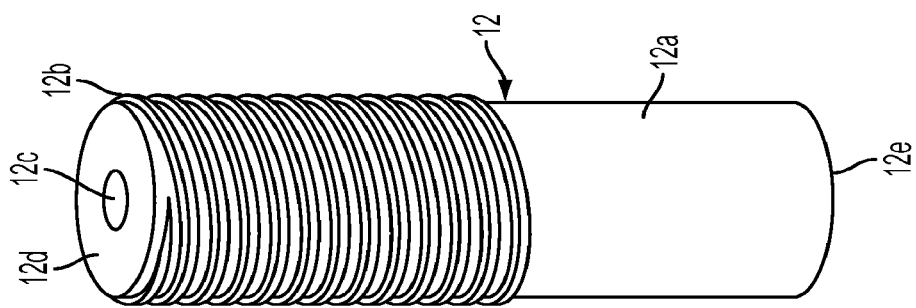
FIG. 3A shows a perspective view of a dowel to be used in the invention described herein.

FIG. 4 shows a threaded screw 14 that has a screw head 14a and threads 14b that acts as a screw to firmly attach the dowel 12 shown in FIGS. 3A and 3B (FIG. 3B also includes the sleeve 10) coaxially to the implant 18 shown in FIG. 2 that is being repaired. The implant 18 already has a threaded female central bore fastener 18b that receives a screw or bolt for attaching the upper portion of the implant to an abutment or crown. The length of the attachment screw 14 is long enough to extend from inside the passage in the dowel 12 well past the end of the dowel 12 for fastening in the implant bore female fastener 18b.

Referring now to FIG. 3A, a dowel 12 is shown. The purpose of the dowel 12 is to aid in the manual mechanical transfer of the sleeve 10 from the dowel 12 to the implant surface 18a being repaired without engaging or touching the sleeve exterior surface 10c. The dowel 12 is also necessary to physically support the soft titanium thin sleeve 10 to prevent the sleeve 10 from collapsing or being deformed in shape during shipping, handling, and installation. The dowel 12 is a rigid cylindrical body having two separate end-to-end central longitudinal passages 12c and 12cc having different diameters extending coaxially from first end 12d to second end 12e. The purpose of the dowel central passages (shown in FIG. 6 and discussed in greater detail below) is to receive an attachment screw 14 (shown in FIG. 4) that allows the dowel 12 to be firmly attached to the top of the implant 18 being repaired during the transfer of the sleeve 10 from the dowel to the implant.

The exterior surface of dowel 12 includes an upper portion that has threads 12b extending from first end 12d to the midsection of the dowel. The lower portion exterior surface 12a of the dowel is smooth. The exterior diameter of the dowel 12 and surface area 12a is sized to receive the inside diameter of surface restoration sleeve 10 (shown in FIG. 1) on the lower portion of dowel surface 12a. The length of the dowel 12 is such that surface area 12a will provide for the total support of the sleeve 10 and the threaded area 12b will provide surface area for threads for a transfer nut used for applying downward pressure on the surface restoration sleeve that creates a pressed fit of the sleeve on the implant surface.

Referring now to FIG. 3B, the dowel 12 shown in FIG. 3A also includes a sleeve 10. The dowel 12 is used in the manual transfer of the sleeve 10 onto an implant surface 18a (not shown in FIG. 3B) that is being repaired, explained in greater detail below. The dowel 12 also acts to support the thin soft titanium alloy cylindrical sleeve 10 because of its fragile nature at all other times starting at the laboratory when the surface restoration sleeve 10 is created.

FIG. 4 shows a threaded screw 14 that acts as a screw to firmly attach the dowel 12 shown in FIGS. 3A and 3B (FIG. 3B also includes the sleeve 10) coaxially to the implant 18 shown in FIG. 2 that is being repaired. The implant 18 already has a threaded female central bore fastener 18b that receives a screw or bolt for attaching the upper portion of the implant to an abutment or crown. The length of the attachment screw 14 is long enough to extend from inside the passage in the dowel 12 well past the end of the dowel 12 for fastening in the implant bore female fastener 18b.

Figure 5:
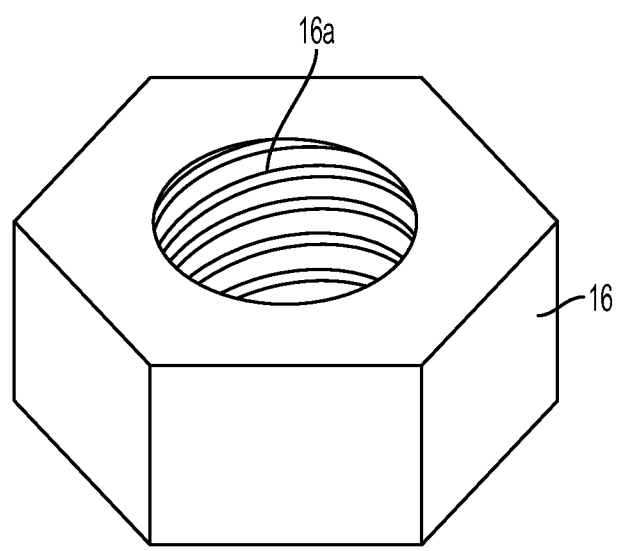
FIG. 5 shows a perspective view of the transfer nut used to manually force the surface restoration sleeve shown in FIG. 1 onto a specific area of the dental implant to be repaired with a dowel.

Referring now to FIG. 5, a surface restoration sleeve transfer nut 16 is shown having a threaded female connector opening 16a that is sized in diameter to engage the threaded upper surface 12b of dowel 12 shown in FIG. 3A and FIG. 3B. In operation the nut 16 is used to transfer the surface restoration sleeve from the dowel 12 to the implant 18. Nut 16 is engaged with a manual tool such as a wrench used by the implant repair dentist to rotate nut 16 on the threaded dowel 12. Manual rotation of the nut 16 moves the nut 16 downwardly on the dowel threads. One side portion of nut 16 presses sleeve 10 downwardly onto the exterior surface of the implant surface 18a to be repaired.

Figure 6:
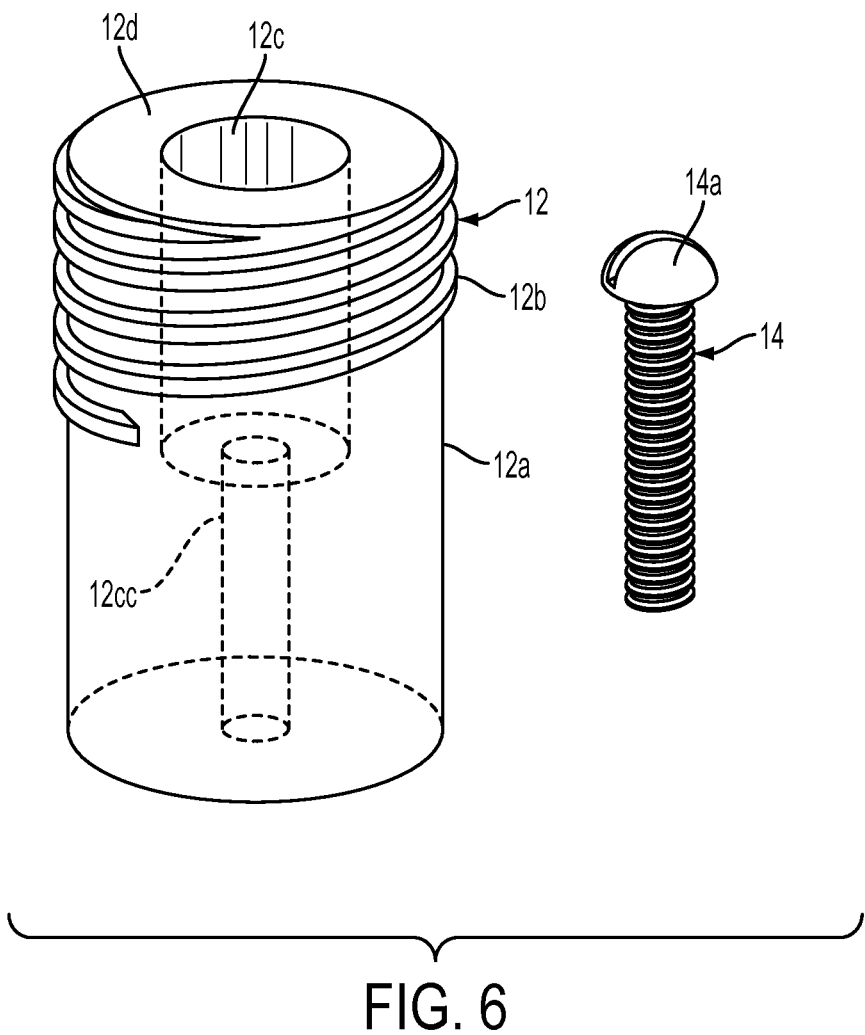
FIG. 6 shows a perspective of the dowel and the attaching screw used to attach the dowel directly to the top of the implant. The attaching screw is placed in the central passage of the dowel. The central passage of the dowel has two separate diameters which are shown dotted in phantom.

FIG. 6 shows a schematic representation of the dowel 12 in order to describe how the dowel 12 is firmly attached to the diseased implant for transfer of a surface restoration sleeve. The dowel 12 has a longitudinal passage that include two coaxial passages 12c and 12cc of different diameters, passage 12c having the larger diameter. An attachment screw 14 having a screw head 14a is manually positioned within the dowel passage segments 12c and 12cc such that the screw head 14a diameter fits in segment 12c but is too large to fit into segment 12cc. However the attachment screw threaded shaft 14b has a diameter that is smaller than the diameter of passage segment 12cc. The attachment screw 14 is fastened to the implant 18 (FIG. 2) and holds the dowel 12 against the top of the implant 18 to be repaired. The implant 18 already has a female threaded bore 18b positioned in the center of the top surface of the implant for receiving the attachment screw.

It is important that the dowel be firmly attached to the implant during the transfer of the sleeve 10 (shown in FIG. 1) to the diseased implant which is accomplished with attachment screw 14 positioned within the passage 12c and passage segment 12cc.

Figure 7:
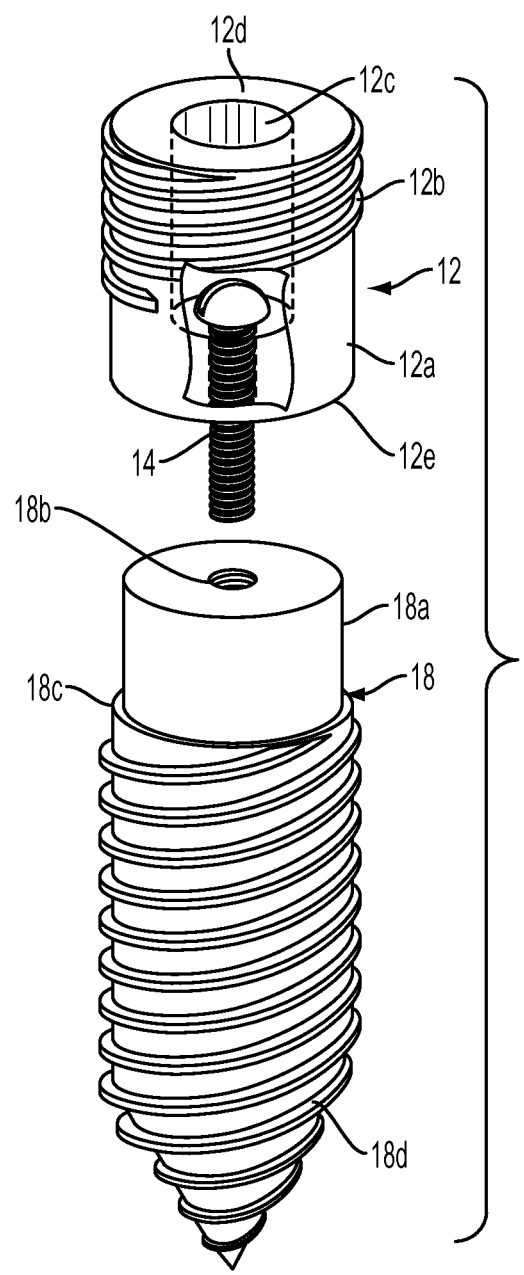
FIG. 7 shows a perspective exploded view of the dowel positioned above the diseased implant coaxially.

FIG. 7 shows the physical relationship between the dowel 12 and the implant 18 in an exploded view. The sleeve 10 is not shown in FIG. 7. The sleeve transfer nut is also not shown in FIG. 7. The attachment screw 14 is shown cutaway inside dowel 12 and is used to firmly attach the dowel 12 to the top surface of implant 18 using the implant female bore threaded opening 18b.

Figure 8:
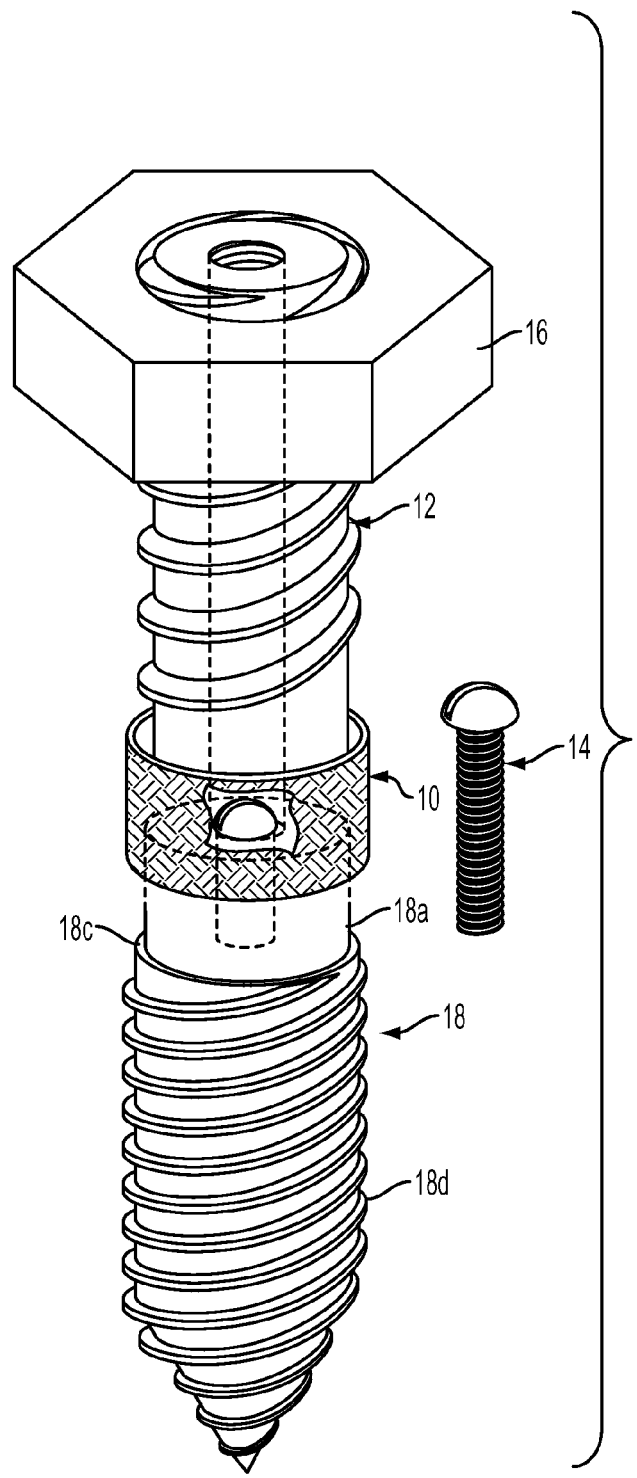
FIG. 8 shows a perspective view of the dowel having a surface restoration sleeve, the dowel being attached to the implant by the attaching screw and the transfer nut threadably attached to the top of the dowel.
Figure 9:
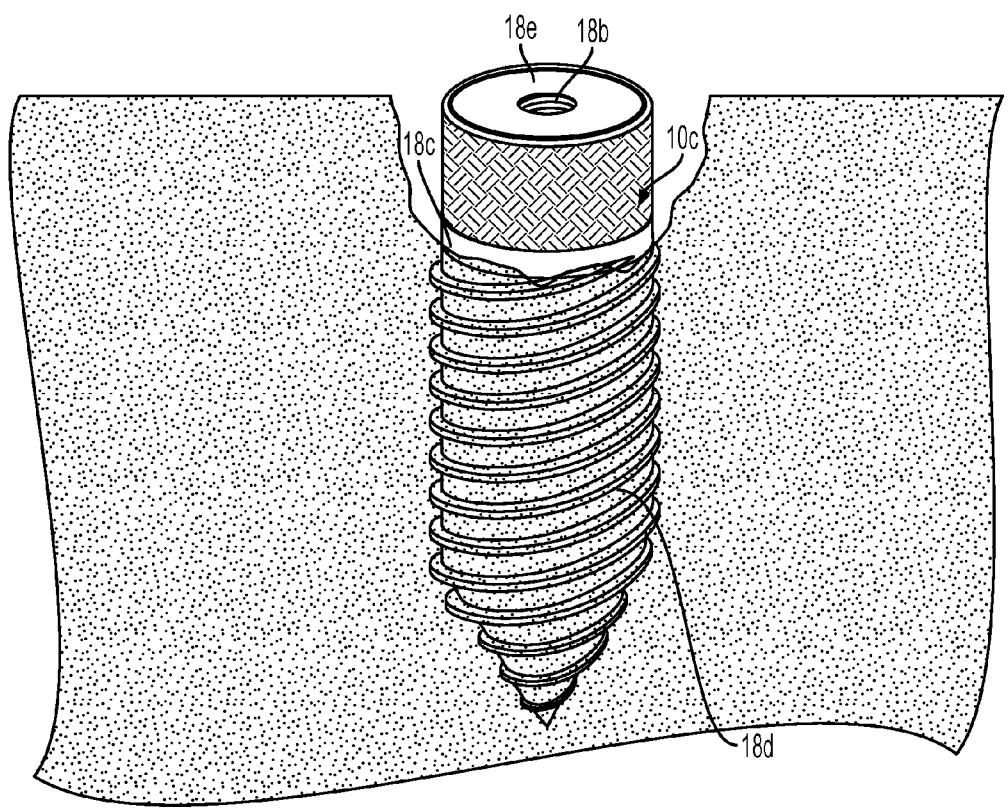
FIG. 9 is a perspective view of an implant after repair with the surface restoration sleeve installed.

The entire device used to transfer a surface restoration sleeve 10 onto a diseased implant 18a is shown in FIG. 8. The implant 18 includes an upper area 18a that, in preparation for the transfer and receipt of the sleeve 10 has had a thin layer of the implant surface 18a removed as evidenced by the implant upper lip 18c. The dowel 12 is firmly attached to the top surface of implant 18 by attachment screw 14 shown cutaway in FIG. 8. The sleeve 10 is shown partially pressed around the upper portion of surface 18a. The transfer nut 16 is threadably attached to the upper threaded portion of dowel 12. Rotating the transfer nut with a tool such as a wrench in a downward direction will allow the transfer nut 16 to engage in the uppermost edge of the surface restoration sleeve 10. Further turning of the transfer nut 16 places downward pressure on the sleeve 10 top edge forcing the sleeve 10 over the previously ground surface area 18a of implant into position until the sleeve 10 completely surrounds the desired area of implant 18a surface, engaging lip 18c when the transfer of the sleeve 10 is complete. Attachment screw 14 is loosened and the dowel 12 is removed from the implant 18 The implant practitioner can then prepare the bone area replacement to enhance osseointegration between the bone and the exterior surface of the replacement sleeve 10 which has been specially prepared.

The method for repairing an implant that has peri-implantitis begins with the preparation of a surface restoration sleeve made of the proper titanium alloy materials, having an exterior surface treated to enhance osseo-integration and sized to fit tightly around the diseased area of the implant upper portion.

The first step from the patient's standpoint is to have a thin layer around the implant ground to remove diseased areas and to expose the repairable surface area of the implant device. The exterior surface 18a of the implant device to be repaired is mechanically treated by grinding to remove a small thin surface layer. The exterior surface of the implant device when ground is reduced to a very specific diameter equal to the inside diameter of the surface restoration sleeve that will then provide a very tight fit of the sleeve that covers the previously diseased area.

A dowel having an upper threaded portion and a lower cylindrical smooth portion is selected.

When applying the sleeve to the implant surface being repaired, it is important that the exterior surface of the sleeve not be touched, which may seriously affect the ability of the t sleeve for osseo-integration. The sleeve is aligned coaxially with the lower base of the dowel and attached to the dowel lower portion without touching the exterior of the sleeve. This union is accomplished in a laboratory in a sterile environment. The unit will be packaged in a sterile container for shipment and storage.

The dowel and surface restoration sleeve once attached are then aligned axially over the implant to be repaired. The attachment screw is placed through the center passage of the dowel and the dowel is firmly affixed to the implant using the female threaded opening in the top of the implant device.

After the dowel, with its previously attached surface restoration sleeve, along with the transfer nut, is aligned with the implant. The central connecting attachment screw which goes through the dowel and engages the implant is placed and screwed into the threaded implant female bore opening. Once the connecting screw is tightened, the dowel and the implant behave as one unit allowing the transfer of the sleeve from the dowel to the implant Rotating the transfer nut on the threads of the dowel will force the sleeve downwardly around the diseased area of the upper portion of the implant, covering the diseased area of the implant to be repaired by the surface restoration sleeve.

After the sleeve is in place on the implant, the connecting screw holding the dowel against the implant is removed as is the dowel.

The implant now has a surface restoration sleeve with a suitable surface area to enhance osseo-integration around the previously diseased implant. The implant is now ready for conventional bone enhancement treatment.

In an alternative method of installation of the surface restoration sleeve, in lieu of a transfer nut for moving the sleeve from the dowel, a sleeve specially treated as described above on the exterior surface could be placed on a dowel and another cylindrical tool placed over the dowel, and then transfer the sleeve with a tapping action that would cause the sleeve to be press fitted on the implant.

And yet in another alternate embodiment for installation and transfer of the sleeve onto the implant in lieu of a transfer nut, a tool that provides leverage having a cylindrical actuator could be used to press manually the sleeve onto the implant.

In another embodiment, the surface restoration sleeve could be made in the shape of a truncated cone. In this case, the implant surface to be repaired would also be ground in a truncated conical shape.

It is to be understood that the invention is not limited in its application to the specific details of construction and the arrangement of the compound set forth in the description or in the drawings.

What is claimed is:

1. The method for repairing a tooth implant having a centrally located female connector, said tooth implant upper exterior surface area portion having been damaged by peri-implantitis comprising the steps of:
  a. creating a surface restoration sleeve having a uniformly round inside diameter that replaces the damaged upper exterior surface area portion of the implant to be removed by grinding in order to enhance osseo-integration;
  a.1 grinding the upper exterior surface area portion of said tooth implant damaged by peri-implantitis that produces a diameter of the implant that is uniformly round to fit the inside diameter of the surface restoration sleeve;
  b. providing a dowel having a central passage axially disposed therein and having an upper portion that include threads for receiving a transfer nut and a lower portion for receiving said surface restoration sleeve;
  c. providing a dowel attaching screw that includes a threaded portion, said screw sized to fit longitudinally and axially through said dowel central passage and attachable to said implant female connector;
  d. attaching said dowel lower portion to said surface restoration sleeve;
  e. attaching said dowel with said surface restoration sleeve aligned along the longitudinal axis of said dowel and said implant using said dowel attaching screw;
  f. providing a transfer nut having a central threaded passage on said upper portion that includes threads of said dowel; and
  g. moving said transfer nut relative to said dowel while engaging one side of said transfer nut against said surface restoration sleeve causing said surface restoration sleeve to be press fitted on the upper portion of said implant.

2. An apparatus for repairing a tooth implant damaged by peri-implantitis, said implant including a central threaded female connector and an upper exterior surface area ground uniformly round to be repaired comprising:
  a surface restoration sleeve sized in diameter to fit snugly around the upper exterior surface area ground uniformly round to be repaired on said implant, said surface restoration sleeve having exterior surface treated for enhanced osseo-integration,
  dowel having a lower exterior surface area sized in diameter to equal the inside diameter of said surface restoration sleeve, for receivably attaching said surface restoration sleeve, and said dowel having an upper exterior surface area that includes fastener threads for receiving a transfer nut and said lower exterior surface area for receiving said surface restoration sleeve; and
  said dowel including a longitudinal central axial passage extending through the dowel from end to end.

3. An apparatus as in claim 2 including:
  an elongated fastener having a head, said fastener including a threaded shaft sized to fit within a portion of the central axial passage of said dowel and sized in length to attach to said implant central threaded female connector, said elongated fastener adapted for attaching said dowel including said surface restoration sleeve to the ground upper exterior surface area portion of said implant.

4. An apparatus as in claim 3, including:
  a transfer nut having a central threaded passage sized in diameter to engage the fastener threads on said upper exterior surface area of said dowel while pressing downwardly on said surface restoration sleeve when said dowel is attached to said implant upper portion by said elongated fastener.

5. An apparatus as in claim 3, wherein:

said dowel central axial passage including a first passage segment having a predetermined diameter larger than said elongated fastener head diameter and a passage end wall surface and a second passage with a smaller diameter than said first passage but large enough to receive the threaded shaft of said elongated fastener with, said elongated fastener head engageable with the end wall surface of said dowel first passage to allow the elongated fastener to hold the dowel firmly in place when the elongated fastener is also connected to said implant.

* * * * *